United States Patent [19]

Goltzer

[11] Patent Number: 4,973,305
[45] Date of Patent: Nov. 27, 1990

[54] METHOD AND APPARATUS FOR INSERTING AND RETAINING AN EPIDURAL CATHETER

[76] Inventor: David Goltzer, 2431 E. Marshall Ave., Phoenix, Ariz. 85016

[21] Appl. No.: 448,072

[22] Filed: Dec. 8, 1989

[51] Int. Cl.$^5$ .............................................. A61M 5/00
[52] U.S. Cl. ..................................... 604/51; 604/101; 604/158
[58] Field of Search ............................ 604/158–162, 604/96, 97, 99, 101, 117, 51

[56] References Cited

U.S. PATENT DOCUMENTS

| | | |
|---|---|---|
| 3,680,544 | 8/1972 | Shinnick et al. . |
| 3,742,960 | 7/1973 | Dye et al. . |
| 3,827,434 | 8/1974 | Thompson et al. . |
| 3,952,742 | 4/1976 | Taylor . |
| 4,453,545 | 6/1984 | Inoue .................................. 604/101 |
| 4,518,383 | 5/1985 | Evans ................................... 604/51 |
| 4,645,491 | 2/1987 | Evans ................................. 604/158 |
| 4,650,472 | 3/1987 | Bates ................................. 604/158 |
| 4,737,146 | 4/1988 | Amaki et al. ........................ 604/51 |
| 4,748,982 | 6/1988 | Horzewski et al. . |
| 4,819,664 | 4/1989 | Nazari ................................. 604/96 |

Primary Examiner—Stephen C. Pellegrino
Attorney, Agent, or Firm—Charles E. Cates

[57] ABSTRACT

A method of making an epidural insertion of a catheter and means for retention therein whereby a double lumen catheter having an air and medication conduit are provided, and the air conduit has a retention balloon at the distal, epidural end and a pilot indicator balloon at the proximal end. The catheter is inserted through a stylet and the balloon is expanded. The stylet (needle) is withdrawn, the catheter temporarily fastened by external means, the balloons deflated, the needle removed, and the epidural balloon reinflated to hold the catheter in place.

12 Claims, 2 Drawing Sheets

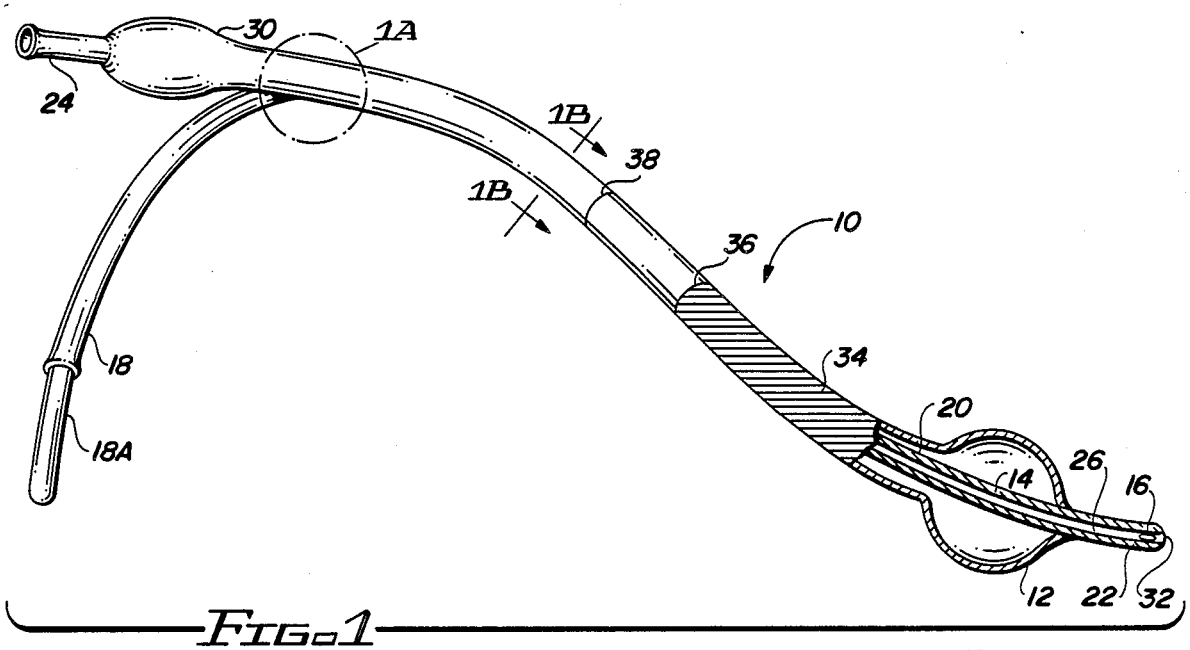
FIG. 1
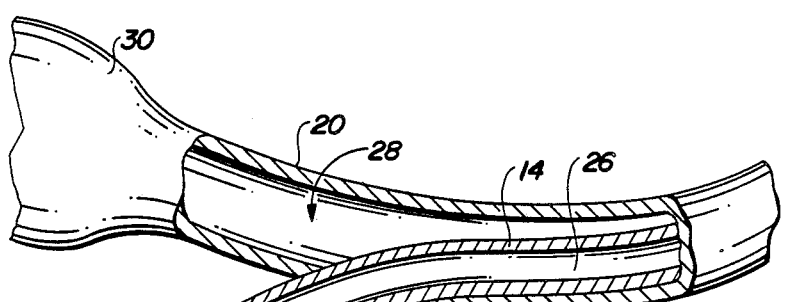
FIG. 1A
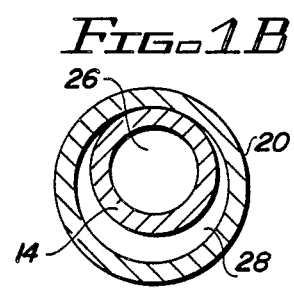
FIG. 1B
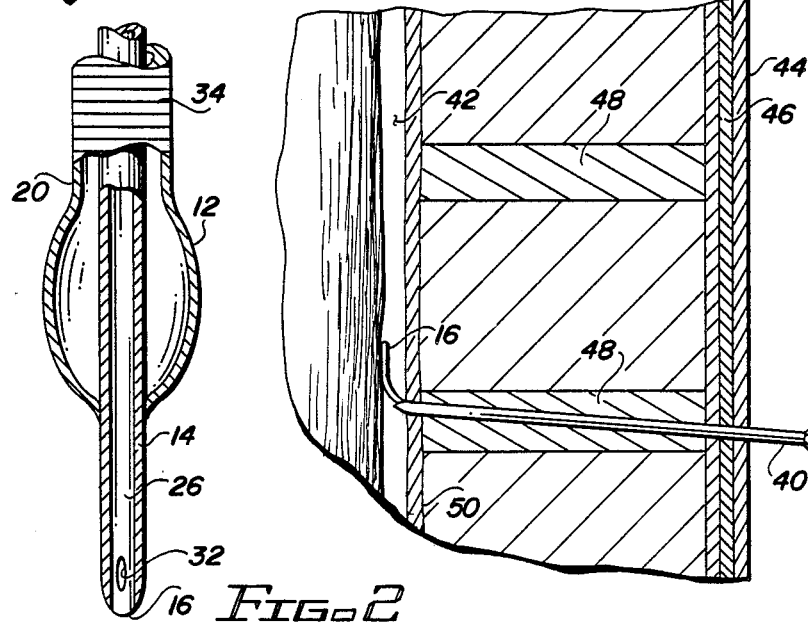
FIG. 2
FIG. 3
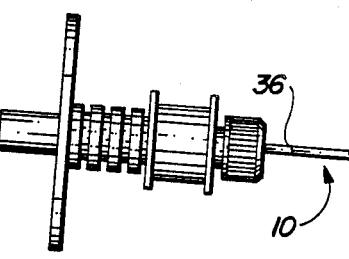
FIG. 9

METHOD AND APPARATUS FOR INSERTING AND RETAINING AN EPIDURAL CATHETER

BACKGROUND OF THE INVENTION

This invention pertains to means and methods for performing prolonged epidural anaesthesia. Epidural anesthesia is a delicate procedure in which the anaesthetist, after precisely locating the epidural space with a needle without encroaching on the dural structure or penetrating an epidural vein, inserts a catheter for the administration of an analgesic or anaesthetic for retention over a period of hours or days, depending on the patient's condition to be treated.

The presently available medical equipment and methods used in such procedures are discussed in "Handbook of Epidural Anaesthesia and Analgesia" published by Grune & Stratton, Inc., Orlando, Fla. 32887.

For other applications, "Fogarty" brand arterial embolectomy catheters, made by American Edwards Laboratories, provide a catheter with a balloon tip to be inflated for the purpose of removing emboli and thrombi from arteries. Shinnick patent U.S. No. 3,680,544 discloses a spinal syringe and needle, fitted with a catheter having an inflatable balloon at its tip. The instrument is designed for insertion through the wall of the heart into the right ventricular cavity. After insertion, the balloon is inflated to prevent displacement of the catheter. When the needle is withdrawn, the catheter remains in place for administering medication to the heart. Taylor patent U.S. No. 3,952,742 discloses a similar device for penetrating the wall of the heart and anchoring the tip of a catheter in place inside the heart by inflating a small balloon. Sheridan/CF (tm) tracheal tube has a pilot balloon whose purpose is to indicate the condition of a retention balloon inserted in a trachea to retain a tracheal tube.

The positioning of the catheter in the epidural space is very important in the epidural anaesthesia process to deliver the anesthetic to the area to be treated, to achieve the purpose of the epidural block. In this connection, excessive movement after positioning of the catheter also produces undesirable effects. Prior art catheter tubes have a high potential for displacement in the epidural space.

While performing epidural anaesthesia it is important not to puncture the dura which borders the epidural space on one side. One precautionary measure used to help prevent damage to the dura is to use a needle such as the standard Tuohy needle that directs the catheter away from the dural area. Even with the use of an appropriate needle, using a prior art epidural catheter can still readily cause damage to the dura because the flow of anaesthesia can be directed toward the dura.

Prior art catheter tubes have utilized narrow blue or black bands regularly spaced along the tube to indicate incremental lengths of tubing. These bands are often confusing and are difficult to read quickly.

Prior art epidural catheters extend from the patient to an external source of medication. They are prone to tangling and are awkward to handle during the insertion of the catheter.

Accordingly, an object of this invention is to provide a means for inserting a catheter in the epidura with minimal movement of the catheter after insertion.

Another object of this invention is to provide an epidural catheter that is easier to visually position.

Still another object of this invention is to provide an epidural catheter that is less likely to cause damage to the dura.

Yet still another object of this invention is to provide an epidural catheter that is less subject to tangling.

Other objects and advantages will become apparent by reference to the following description and drawings.

SUMMARY OF THE INVENTION

The present invention relates to an apparatus and method for introducing into and maintaining a catheter in a patient's epidural space. I have discovered that a balloon may be used to anchor an epidural catheter securely in place for extended lengths of time without interfering with any necessary natural functions. The catheter of this invention, first being shortened to a manageable first stage length that does not readily tangle, is introduced into the patient's epidural space by means of a hollow needle, sized to receive the catheter, that is adapted for puncturing the epidural space. A second stage of the catheter is used as an extension of the first stage to provide a connection between the first stage and a remote source of medication. The first stage, sized to fit the bore in the needle, has a broad band of brightly colored indicia which may be red. The indicia is preferably solid (continuous) and marks the length of the needle relative to the epidural end of the catheter.

The catheter has an epidural end and an attachment end. Spaced (about 1 to 3 inches, preferably 2 inches) from the epidural end of the catheter and operatively attached to the first stage of the catheter is a retention balloon which communicates with a pilot balloon outside the patient's body. The latter serves to indicate whether or not the retention balloon is inflated.

In accordance with the present invention, the first stage catheter may be from about ten inches to about 20 inches, but preferably 15 inches in length.

The first color segment preferably is equal to the length of the needle and may define a segment of the catheter immediately behind the retention balloon toward the attachment end. This segment is used to signal that the end of the catheter has reached the top of the needle or some point past the end of the needle, as desired. Further toward the attachment end are narrower conventional marking bands to indicate incremental distances.

The dural arc is sensitive and may be damaged by medication flowing directly at it. If the delivery aperture is positioned away from the dura after insertion, damage is less likely to occur. Accordingly, the epidural end of the catheter preferably is curved, having a side aperture to direct flow of medication out of the catheter on a path not parallel to the catheter. The positioning of the aperture also provides a means for directional flow.

The apparatus described above may be used in conjunction with the following method of performing an epidural block. The first step is to insert the introducing needle into the epidural space. The catheter is then inserted through the needle into the epidural space. The correct placement of the catheter in the needle in the epidural space is determined with reference to colored indicia carried on the catheter. The catheter is fed into the epidural space to the appropriate location by visualizing colored measurement indicia on the catheter, conveniently, a brightly colored broad band which is no longer visible when the catheter has reached the tip of the needle. The catheter may be further fed into the bore of the needle and the additional bands may be used to indicate how far past the needle the tip of the catheter has progressed.

The catheter has an inflatable epidural balloon near its epidurally inserted end and a pilot balloon outside the patient's body which is in fluid communication with the epidural balloon. The latter is inflated to retain the catheter in place, and the pilot balloon is visually inspected to verify that the epidural balloon is inflated.

The needle is then withdrawn from the epidural space, after which the catheter may be temporarily fastened into place. The pilot balloon may then be deflated to remove the needle from the catheter. Finally, the external end of the catheter is attached to a source of medication.

BRIEF DESCRIPTION OF THE DRAWINGS

In order that the invention may be better understood, a description of the invention is provided herein with reference to the general concepts and an illustrative embodiment thereof, wherein:

FIG. 1 is a perspective view of a presently preferred embodiment of the catheter to be used for performing epidural anaesthesia;

FIG. 1A is a portion IA of FIG. 1, greatly enlarged, and partially sectioned;

FIG. 1B is a cross section of FIG. 1 taken along the sight of 1B—1B;

FIG. 2 is an enlarged view of the retention balloon at the tip of the catheter shown in FIG. 1;

FIG. 3 is a diagrammatic view in cross section between a portion of the spinal column of a patient, showing in accordance with this invention the catheter inserted with the needle into the epidural space;

FIG. 9 is an enlarged view of the alternative embodiment of the retention balloon at the tip of the catheter.

DESCRIPTION OF THE PREFERRED EMBODIMENT

Figure 4:
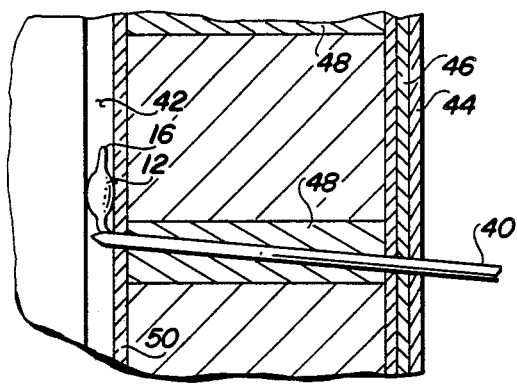
FIG. 4 is a diagrammatic view of FIG. 5 showing the catheter inserted with the use of a needle into the epidural space with the retention balloon inflated.

The description of the preferred embodiment set forth hereafter concerns a double-lumen epidural catheter with the tubes being concentric, one within the other. However, multi-lumen epidural catheters of other architectures may be employed.

Referring now to FIGS. 1-2, catheter 10 having has an inner medication tube 14 with a distal tip 16 and proximal portion 18 forming a conduit 26 for an anaesthetic solution and an outer air tube 20 terminating in balloon 12.

At the proximal or attachment end of the catheter 10, the inner 14 and outer 20 tubes are split. At the proximal end 24 of the outer tube 20 is a pilot balloon 30. The tube at the proximal end 24 of the pilot balloon 30 is flanged and adapted for the insertion of a specially made syringe. Via the syringe, air enters into the proximal end 24 of the outer tube 20 into the pilot balloon 30, through the conduit 28 of the outer tube 20 and into the retention balloon 12 at the distal end thus inflating both balloons. The pilot balloon 30 will remain inflated as long as the retention balloon 12 is inflated providing an indicator for the condition of the retention balloon 12.

The inner tube 14 at the proximal end 18 is flanged, allowing a catheter extension to be attached. The extension makes the catheter long enough to reach the source of medication. By providing a means for extending the catheter, the catheter that is inserted can be made a manageable length that is not readily entangled.

At the distal tip 16 of the inner tube 14, there is an aperture 32 through which the medication flows. The aperture 32 is not located at the end of the tube but instead on the side to provide a means for directional flow. If the delivery aperture is positioned away from the dura after insertion, damage is less likely to occur to the dura.

A broad red band 34 that is of the same length as the length of the needle is appropriately located on the tube. The length of the band 34 is used to signal the position of the catheter and when the band disappears the end of the catheter has reached the tip of the needle. Further up the catheter are additional bands 36-38 that can be used to indicate how far past the needle the tip of the catheter has progressed.

FIGS. 3-6 are a series of views depicting the catheter in use in accordance with the present invention. In FIG. 3, an epidural needle 40 is introduced into the epidural space slowly and gradually. The needle 40 used to locate the catheter 10 in the epidural space 42 passes successively through the skin 44, subcutaneous tissue 46, interspinous ligament 48 and ligamentum flavum 50 to finally reach the epidural space 42. After epidural placement of the needle 40 has been assured, the epidural catheter 10 is then introduced into the epidural space 42 through the needle 40. The epidural catheter 10 is inserted a desired distance into the epidural space 42. The necessary distance is known to have been achieved by observing the location of the broad red band 34 and subsidiary bands 36 and 38 on the catheter 10.

In FIG. 4 air is injected into the proximal end 24 of the outer tube 20 causing the retention balloon 12 to inflate. The inflated retention balloon 12 allows the needle 40 to be withdrawn without fear that the catheter will be dislodged.

Figure 5:
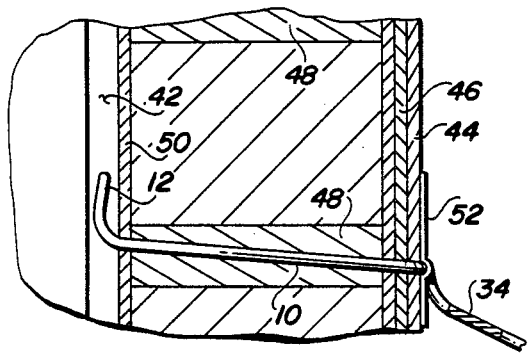
FIG. 5 is a diagrammatic view of the spinous processes showing the catheter temporarily fastened in place and the needle withdrawn.

After the needle is withdrawn from the patient, the catheter is temporarily attached in place with, for example, adhesive tape 52 as shown in FIG. 5. The pilot balloon 30 is then deflated to allow the needle 40 to be removed from the catheter 10.

Figure 6:
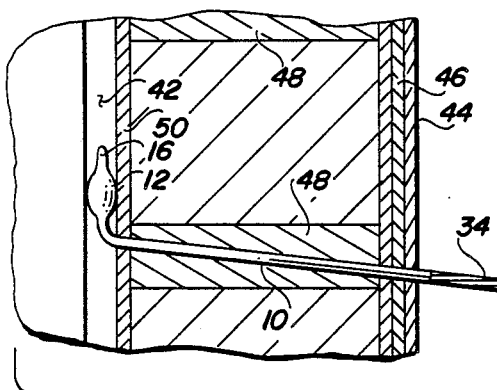
FIG. 6 is a diagrammatic view of the spinous processes showing the catheter with the retention balloon and pilot balloon inflated and the external end of the catheter attached to a source of medication.

After the needle 40 has been removed, the retention balloon 12 and the pilot balloon 30 are again inflated as shown in FIG. 6. A clamp 54 engages and seals the proximal end 24 of the outside tube to prevent the escape of air from the balloons 12 and 30. The temporary adhesive tape 52 is now removed The catheter extension is attached to the proximal end 18 of the inner tube to permit the injection of medication into the epidural space 42. In this embodiment it is recommended that a catheter having a non-kinking lumen be used. An example of a non-kinking catheter can be obtained from Arrow International, Inc., Reading, Pa. 19610.

Figure 7:
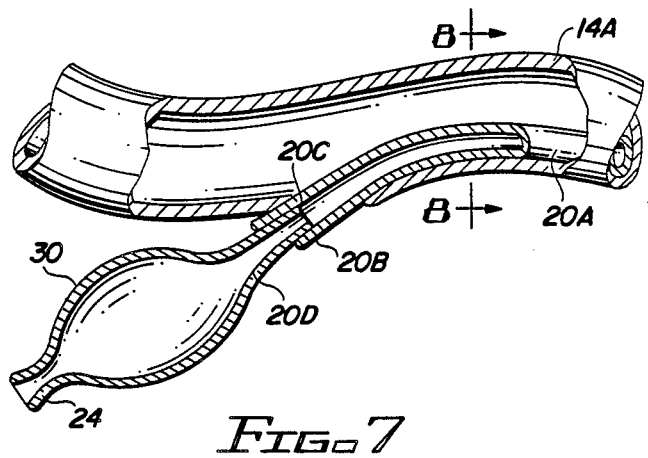
FIG. 7 is an alternative embodiment of that portion of FIG. 1 corresponding to FIG. 1A.
Figure 8:
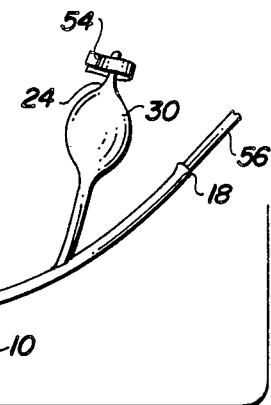
FIG. 8 is a cross section, greatly enlarged, of FIG. 7 taken along the line 8—8.

An alternative embodiment is shown in FIG. 7 wherein the pilot balloon 30 is detachable from the air tube 20a which can be placed inside the medication tube 14a. The tube 20a has a slightly flared mouth 20b to receive a force fit of the end 20c of the pilot balloon extension tube 20d. Thus, the pilot balloon 30 can be removed to permit the facile removal of the needle 40 from the catheter. For convenience a list of the various elements and their identifying members are provided below:

- 10: catheter
- 12: retention balloon
- 14: inner medication tube
- 14a: medication tube
- 16: distal tip
- 28: proximal end
- 20: outer air tube
- 20a: air tube
- 20b: flared mouth
- 20c: end
- 20d: balloon extension tube
- 24: proximal end
- 26: conduit
- 28: conduit
- 30: pilot balloon
- 32: aperture
- 34: band
- 36: band
- 38: band
- 40: epidural needle
- 42: epidural space
- 44: skin
- 46: subcutaneous tissue
- 48: interspinous ligament
- 50: ligamentum flavum
- 52: adhesive tap
- 54: clamp
- 56: catheter extension While representative presently preferred embodiments of the invention are disclosed above, the invention encompasses various equivalent structures and functions as distinctly claimed and pointed out in claims appended hereto.

What is claimed is:

1. Apparatus for introducing into and maintaining a catheter in a patient's epidural space comprising:
   a. a hollow needle having means adapted for the puncture of an epidural space and a bore sized to permit the introduction of a catheter through said bore into the patient's epidural space;
   b. a two-stage catheter having
      (1) a shortened first stage sized to fit said bore;
      (2) an epidural end and an attachment end; and
      (3) brightly colored indicia, marking the length of said needle relative to the epidural end of said catheter;
   c. a retention balloon operatively attached at said epidural end, a pilot balloon disposed to operate outside the patient's body and having fluid communication with said retention balloon; and
   d. means for attaching said catheter to the source of medication.

2. The apparatus of claim 1 wherein the length of said first stage catheter is from about ten inches to about twenty inches in length.

3. The apparatus of claim 2 wherein the length of said first stage catheter is about fifteen inches in length.

4. The apparatus of claim 1 wherein the retention balloon is spaced from the epidural end of said catheter about 1 to 3 inches.

5. The apparatus of claim 4 wherein the retention balloon is spaced from the epidural end of said catheter about 2 inches.

6. The apparatus of claim 1 wherein said first color segment is equal to the length of said needle and defines a segment of the catheter immediately behind said retention balloon toward the attachment end.

7. The apparatus of claim 1 wherein the epidural end of said catheter is curved having an aperture located such that flow of medication out of said catheter is directed in a path which is not parallel to the catheter.

8. The apparatus of claim further comprising extension means to connect the catheter to a remote source of medication.

9. A method of performing an epidural block comprising the steps of:
   a. inserting an introducing needle into the epidural space;
   b. inserting through the needle into the epidural space a catheter having an inflatable epidural balloon near its epidurally inserted end and a pilot balloon in fluid communication with the epidural balloon;
   c. inflating the epidural balloon to retain the catheter in place and verifying inflation by visually inspecting the pilot balloon;
   d. withdrawing the needle; and
   e. attaching the external end of the catheter to a source of medication.

10. The method of claim 9 further comprising the step of determining the correct placement of the catheter in the needle in the epidural space with reference to colored indicia carried on the catheter.

11. The method of claim 9 further comprising the step of feeding the catheter into the epidural space by visualizing colored measurement indicia on the catheter.

12. A method of performing an epidural block comprising the steps of:
   a. inserting an introducing needle into the epidural space;
   b. inserting through the needle into the epidural space a catheter having an inflatable epidural balloon near its epidurally inserted end and a pilot balloon in fluid communication with the epidural balloon;
   c. temporarily fastening the catheter in place and deflating the said balloons to permit withdrawal of said needle;
   d. withdrawing said needle from said catheter; and
   e. reinflating said balloons.

* * * * *